(12) United States Patent
Huang et al.

(10) Patent No.: US 12,173,283 B2
(45) Date of Patent: Dec. 24, 2024

(54) CELL MODEL FOR IN VITRO EVALUATION OF COMPOUND-INDUCED SKIN SENSITIZATION AND A CONSTRUCTING METHOD THEREFOR

(71) Applicant: South China University Of Technology, Guangdong (CN)

(72) Inventors: Lizhen Huang, Guangdong (CN); Guorui Zhong, Guangdong (CN); Haojian Li, Guangdong (CN); Shuilin Xie, Guangdong (CN); Shihui Pang, Guangdong (CN); Jing Bai, Guangdong (CN); Changsheng He, Guangdong (CN); Xinyi Du, Guangdong (CN); Qixiao Zhang, Guangdong (CN); Haijie Wang, Guangdong (CN); Hongli Du, Guangdong (CN)

(73) Assignee: South China University Of Technology, Guangdong (CN)

( * ) Notice: Subject to any disclaimer, the term of this patent is extended or adjusted under 35 U.S.C. 154(b) by 1379 days.

(21) Appl. No.: 16/611,818

(22) PCT Filed: Oct. 29, 2018

(86) PCT No.: PCT/CN2018/112411
§ 371 (c)(1),
(2) Date: Nov. 7, 2019

(87) PCT Pub. No.: WO2019/114439
PCT Pub. Date: Jun. 20, 2019

(65) Prior Publication Data
US 2020/0140856 A1    May 7, 2020

(30) Foreign Application Priority Data
Dec. 14, 2017 (CN) .......................... 201711335463.3

(51) Int. Cl.
| | |
|---|---|
| *C12N 15/11* | (2006.01) |
| *A01K 67/0278* | (2024.01) |
| *C12N 5/071* | (2010.01) |
| *C12N 5/0784* | (2010.01) |
| *C12N 5/0786* | (2010.01) |
| *C12N 9/22* | (2006.01) |
| *C12N 15/85* | (2006.01) |
| *C12Q 1/6897* | (2018.01) |

(52) U.S. Cl.
CPC .......... *C12N 15/11* (2013.01); *A01K 67/0278* (2013.01); *C12N 5/0629* (2013.01); *C12N 5/0639* (2013.01); *C12N 5/0645* (2013.01); *C12N 9/22* (2013.01); *C12N 15/85* (2013.01); *C12Q 1/6897* (2013.01); *C12Y 114/99003* (2013.01); *C12N 2015/8527* (2013.01); *C12N 2015/859* (2013.01); *C12N 2310/20* (2017.05); *C12N 2503/02* (2013.01); *C12N 2510/00* (2013.01); *C12N 2800/80* (2013.01)

(58) Field of Classification Search
CPC .... C12N 15/11; C12N 15/85; C12N 2310/20; C12N 2510/00; C12N 2800/107; C12N 2800/80; C12N 2810/10; C12N 5/0629; C12N 5/0639; C12N 5/0645; C12N 9/22; C12N 15/90; C12N 15/907; C12N 2015/8527; C12N 2015/859; C12N 2502/99; C12N 2503/00; C12N 2503/02; G01N 33/5047; G01N 33/5044; G01N 33/5008; C12Y 114/99003; C12Q 1/6897
See application file for complete search history.

(56) References Cited

FOREIGN PATENT DOCUMENTS

| | | |
|---|---|---|
| CN | 107106628 A | 8/2017 |
| CN | 108103098 A | 6/2018 |
| WO | WO2017/044864 A1 | 3/2017 |

OTHER PUBLICATIONS

Roger Emter et al. Toxicology and Applied Pharmacology, vol. 288, No. 3, Nov. 1, 2015 (Nov. 1, 2015), pp. 281-288, see abstract, and p. 282. (Year: 2015).*

Dan Xiao et al., A novel luciferase knock-in reporter system for studying transcriptional regulation of the human Sox2 gene, Journal of Biotechnology, vol. 219, Feb. 10, 2016 (Feb. 10, 2016), pp. 110-116, see abstract, pp. 111-114. (Year: 2016).*

(Continued)

*Primary Examiner* — Janet L Epps -Smith
(74) *Attorney, Agent, or Firm* — LOZA & LOZA, LLP; Michael F. Fedrick (57) ABSTRACT

A cell model for in vitro evaluation of compound-induced skin sensitization and a constructing method therefor. The method for constructing the cell model comprises the steps of: designing and constructing an sgRNA expression vector based on CRISPR/Cas9 vector system; designing and constructing a homologous recombinant vector capable of knocking a reporter gene linked to a self-cleaving peptide sequence into a specific site of the expression frame of the HMOX1 gene; co-transfecting the homologous recombinant vector, an hCas9 plasmid and the sgRNA expression vector into a cell, and carrying out monoclonal expansion to obtain the cell model. The present invention obtains a HaCaT cell model in which a luciferase gene is knocked in before the stop codon of the HMOX1 gene by combination of CRISPR/CAS9 and a monoclonal cell technique. The cell model realizes synchronous expression of the luciferase gene and the HMOX1 gene, thereby effectively distinguishing sensitizing compounds from non-sensitizing compounds.

7 Claims, 5 Drawing Sheets
Specification includes a Sequence Listing.

(56) References Cited

OTHER PUBLICATIONS

WIPO, Chinese International Search Authority, International Search Report mailed Feb. 1, 2019 in International Patent Application No. PCT/CN2018/112411, 7 pages.
Xiao, Dan et al., "A Novel Luciferase Knock-In Reporter System for Studying Transcriptional Regulation of the Human Sox2 Gene," Journal of Biotechnology, vol. 219, Feb. 10, 2016, pp. 110-116, 7 pages.
Emter, R. et al., "Dual Regulation of Skin Sensitizer-Induced HMOX1 Expression by Bach1 and Nrf2: Comparison to Regulation of the AKRIC2-ARE Element in the KeratinoSens Cell Line," Toxicology and Applied Pharmacology, vol. 288, No. 3, Nov. 1, 2015, pp. 281-288, 8 pages.

\* cited by examiner

CELL MODEL FOR IN VITRO EVALUATION OF COMPOUND-INDUCED SKIN SENSITIZATION AND A CONSTRUCTING METHOD THEREFOR

RELATED APPLICATIONS

This application is the U.S. National Phase of and claims priority to International Patent Application No. PCT/CN2018/112411, International Filing Date Oct. 29, 2018, entitled In Vitro Evaluation Cell Model For Compound-Induced Skin Sensitization And Construction Method Therefor; which claims benefit of Chinese Application No. CN201711335463.3 filed Dec. 14, 2017; both of which are incorporated herein by reference in their entireties.

A sequence listing in compliance with 37 CFR 1.824(a)(2)-(6) and (b) (ASCII text file) entitled 23087-306US_2019-12-10_REVISED_Sequence_Listing.txt, 12,985 bytes, created on Tuesday, Dec. 10, 2019, 12:16:27 PM, is incorporated by reference in this application.

TECHNICAL FIELD

The invention relates to the technical field of genetic engineering, specifically to a cell model for in vitro evaluation of compound-induced skin sensitization and a constructing method therefor, and more specifically to a method for constructing a cell model where a reporter gene is targetedly knocked into a HMOX1 gene mediated by CRISPR/CAS9.

BACKGROUND ART

Skin sensitization is a delayed hypersensitivity reaction caused by skin contact inducers. A sensitizing compound binds to a endogenous protein to form a hapten leading to activation of dendritic cells and a series of keratinocyte reactions, which in turn activate T cells to cause lymph node hyperplasia and skin inflammatory response. This process is also called an adverse outcome path (AOP) of skin sensitization.

Animal experiments studying skin sensitization mainly include Guinea pig maximization test (GPMT) and mouse local lymph node assay (LLNA), in which tracer modified version of LLNA: BrdU ELISA has become the most widely used global standard method, and is currently a mainstream method for evaluation of skin sensitization in China. However, considering that the continuous international promotion of experimental animal welfare ethics and 3R principles, and that animal skin reaction differs from that of human, development of in vitro skin sensitization evaluation methods to replace the animals is imminent. Since adverse outcome path (AOP) of skin sensitization is already clear, currently development of a system model for simulating in vivo sensitization process based on key steps of AOP is a basic strategy for developing an alternative in vitro method. In order to simulate the key events of cell response in sensitization process, establishment of a luciferase reporter cell model is an important means to estimate the accuracy and efficiency of sensitization and achieve high throughput.

At present, keratinocyte and dendritic cell activation pathways are two widely recognized reporter cell models, including KeratinoSens™, LuSens, CellSensor® ARE-bla HepG2, HMOX1-Luciferase and other models specific for the Keap1-Nrf2-ARE pathway as well as THP-G8 cells that may evaluate IL-8 expression, wherein KeratinoSens™ has become the guideline of OECD, and LuSens and THP-G8 have also been admitted by ECVAM. The above reporter cell models indirectly indicate target gene expression by luciferase expression through a combination of a target gene regulatory element and a luciferase gene. The regulatory element of KeratinoSens™ cells is the combination of SV40 and an ARE element of a human AKR1C2 gene. Similarly, the ARE regulatory element of LuSens cells is derived from a rat NQO1 gene. The accuracy of the two cell models can be as high as 75-96% and 71-85%, respectively. A similar method to track IL-8 expression by THP-G8 cell was as high as 82%. The detection accuracy of some cell models is even higher than that of LLNA, indicating that using AOP-based reporter cell is an effective in vitro alternative to LLNA.

However, these reporter cell models only indirectly reflect target gene expression and are incapable of reflecting real-time reporter gene expression. The model is essentially a transgenic cell in which a regulatory element-luciferase is randomly inserted. Although the cell can indirectly evaluate the expression of the target gene by luciferase expression to some extent, it is not a reporter cell that may simultaneously track the expression of the endogenous gene, leading the model to be only available for evaluating sensitization of a compound, without quantitatively evaluating the sensitization strength.

SUMMARY OF THE INVENTION

In order to overcome the deficiencies and disadvantages of the prior art, a primary object of the present invention is to provide a method for constructing a cell model where a reporter gene is targetedly knocked into a HMOX1 gene mediated by CRISPR/CAS9.

Another object of the invention is to provide the cell model where a reporter gene is targetedly knocked into a HMOX1 gene mediated by CRISPR/CAS9.

A further object of the invention is to provide a use of the cell model where a reporter gene is targetedly knocked into a HMOX1 gene mediated by CRISPR/CAS9.

The objects of the invention are achieved by the following technical solutions:

A method for constructing a cell model where a reporter gene is targetedly knocked into a HMOX1 gene mediated by CRISPR/CAS9 comprises the following steps:
(1) designing and constructing an sgRNA expression vector specific for a target site on the HMOX1 gene using CRISPR/Cas9;
(2) designing and constructing a homologous recombinant vector capable of knocking a reporter gene linked to a self-cleaving peptide sequence into a specific site of the expression frame of the HMOX1 gene;
(3) co-transfecting the homologous recombinant vector, an hCas9 plasmid and the sgRNA expression vector into a mammalian keratinocyte, a mammalian dendritic cell or a mammalian monocyte, and carrying out monoclonal expansion to obtain the cell model where a reporter gene is targetedly knocked into a HMOX1 gene mediated by CRISPR/CAS9.

Preferably, the sequence of the sgRNA in step (1) is as shown by SEQ ID NO: 1 or SEQ ID NO: 3.

Preferably, in step (1), the sgRNA is expressed using a U6 promoter, and the designed sgRNA sequence is used to synthesize an Oligo to construct the sgRNA expression vector.

Preferably, the reporter gene in step (2) is one of a luciferase gene, a chloramphenicol acetyltransferase gene (cat), a β-galactosidase gene (LacZ) or a dihydrofolate reductase gene.

Preferably, the self-cleaving peptide in step (2) is a T2A peptide, an E2A peptide, an F2A peptide or a P2A peptide, etc.

Preferably, the specific site in step (2) is located between No. 17529 base and No. 17530 base of the HMOX1 gene, but the site is not limited thereto.

The HMOX1 gene refers to the HMOX1 gene with a non-coding region and an NCBI accession number of NG_023030.

Preferably, the sequence of the homologous recombinant vector in step (2) is as shown by SEQ ID NO: 4.

Preferably, the mammalian keratinocyte in step (3) is a HaCaT cell, but the choice is not limited thereto.

Preferably, the mammalian dendritic cell in step (3) is a CD34-derived dendritic cell, but the choice is not limited thereto.

Preferably, the mammalian monocyte in step (3) is a THP-1 cell, but the choice is not limited thereto.

A cell model where a reporter gene is targetedly knocked into a HMOX1 gene mediated by CRISPR/CAS9 is obtained through the above constructing methods.

The cell model is used in recognizing sensitization of a compound.

The mechanism of the invention is:

Based on transcriptome data of skin-sensitized cells reported in the literature and the internationally admitted skin sensitization reporter cell models, the HMOX1 gene was selected as a target gene for the keratinocyte level response of the AOP pathway. With the development of the CRISPR/Cas9 genome editing technique in recent years, the efficiency of editing a specific site of a genome has been significantly improved. Therefore, the luciferase reporter gene can be inserted into a specific site of the expression frame of the endogenous target gene, so that the luciferase reporter gene can be expressed with the expression of the target gene, thereby achieving real-time reporting of the endogenous target gene expression and evaluating skin sensitization reaction more accurately.

The present invention has the following advantages and effects over the prior art:

The present invention obtains a HaCaT cell model in which a luciferase gene is knocked in before the stop codon of the HMOX1 gene by a combination of CRISPR/CAS9 and a monoclonal cell technique. The cell model realizes simultaneous expression of the luciferase gene and the HMOX1 gene, thereby effectively distinguishing a sensitizing compound from a non-sensitizing compound, and providing a more specific and sensitive cell model for studying sensitization of a compound.

DETAILED DESCRIPTION OF THE EMBODIMENTS

The present invention will be further described in detail below with reference to the embodiments and drawings, but the embodiments of the present invention are not limited thereto.

The tests without specific experimental conditions in the following examples are usually carried out according to conventional experimental conditions or according to the experimental conditions recommended by the manufacturers.

Example 1

In the present invention, a method for constructing a cell model where a reporter gene is targetedly knocked into a HMOX1 gene mediated by CRISPR/CAS9 used for non-diagnostic or non-treating purpose comprises the following steps:

1. Target-site-specific sgRNA for HMOX1 gene was designed, its expression vector was constructed, and its target cleavage efficiency was detected.

Specific sgRNA near the stop codon of HMOX1 gene (NCBI accession number: NG_023030 HMOX1) was designed, and off-target analysis was performed to screen three sgRNAs with good specificity and low possibility of off-target. The results are shown in Table 1.

TABLE 1

| Sequence of the specific sgRNA | | |
|---|---|---|
| name | sgRNA sequence (5'-3') | Genome position |
| sgRNA-1 | TTAACAGGTGGGCGTGCATCAGG | Exon 5 |
| sgRNA-10 | GGTCCTTACACTCAGCTTTCTGG | Exon 5 |
| sgRNA-13 | GCTTTATGCCATGTGAATGCAGG | Exon 5 |

U6 promoter was used to express the sgRNA, and the designed sgRNA sequence was used to synthesize an Oligo to construct a sgRNA expression vector pU6-sgRNA. The sequencing analysis revealed that the construction was successful. The specific method is as follows:

Construction of the U6-sgRNA Plasmid (1) The designed sgRNA was used to synthesize the Oligo, sense strand (i.e., the same sequence as the target site): 5'-CACC-GN19-3', antisense strand: 5'-AAAC-19NC-3' (antisense strand N19 was a reverse complement of the sense strand N19);

(2) The Oligo was annealed; U6 was subjected to BbsI digestion and linearization, and reacted at 37° C. for 2 h, then the linearized fragment was recovered by gel extraction;

(3) The annealed Oligo was ligated to the linearized U6 digestion product overnight; the ligated product was transformed into *E. coli* DH5α competent cells, which were then plated on LB plates containing kanamycin; single colonies were picked and placed in 1 mL LB liquid medium (containing kanamycin), and cultured at 37° C. for 2-3 h; after that, PCR was carried out for the colonies using sp6 primer and sense chain, wherein a sequencing analysis was conducted for positive monoclonal bacteria after PCR of the colonies. Those with the correct sequence were subjected to expansion and plasmid preparation.

Figure 1:
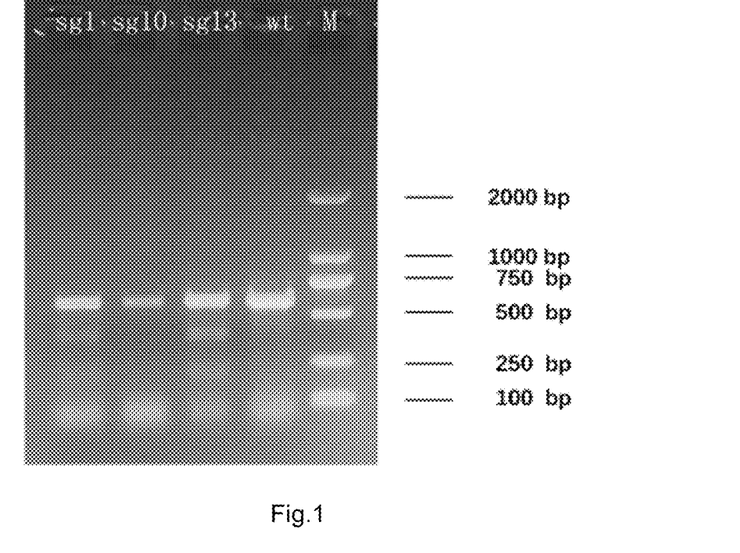
FIG. 1 shows the identification result of target site cleavage by sgRNA using T7E1 digestion method.
Figure 2:
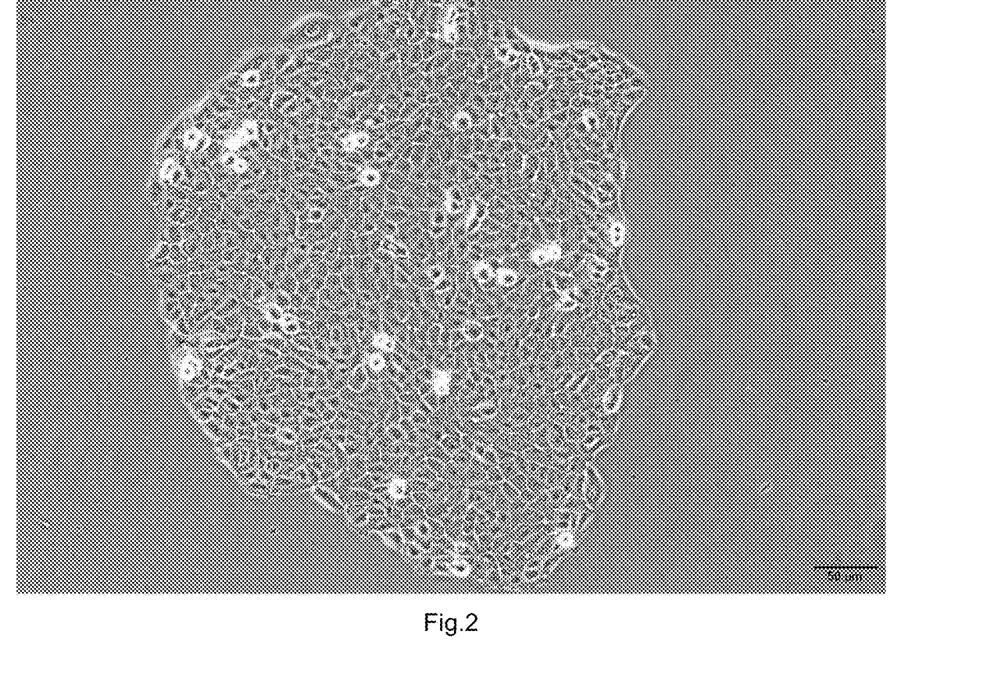
FIG. 2 is a schematic diagram of the HaCaT monoclonal cell (No. 6).
Figure 3:
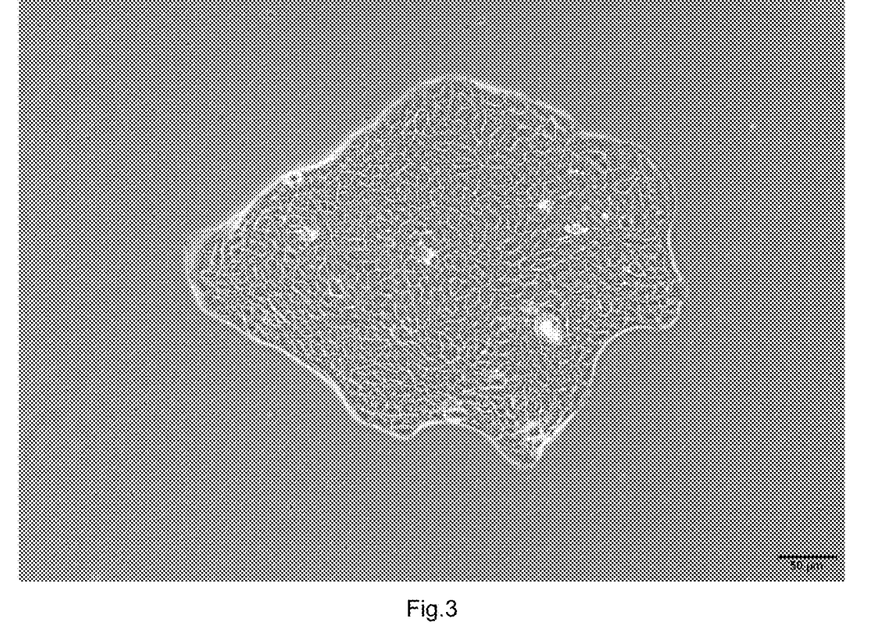
FIG. 3 is a schematic diagram of the HaCaT monoclonal cell (No. 8).
Figure 4:
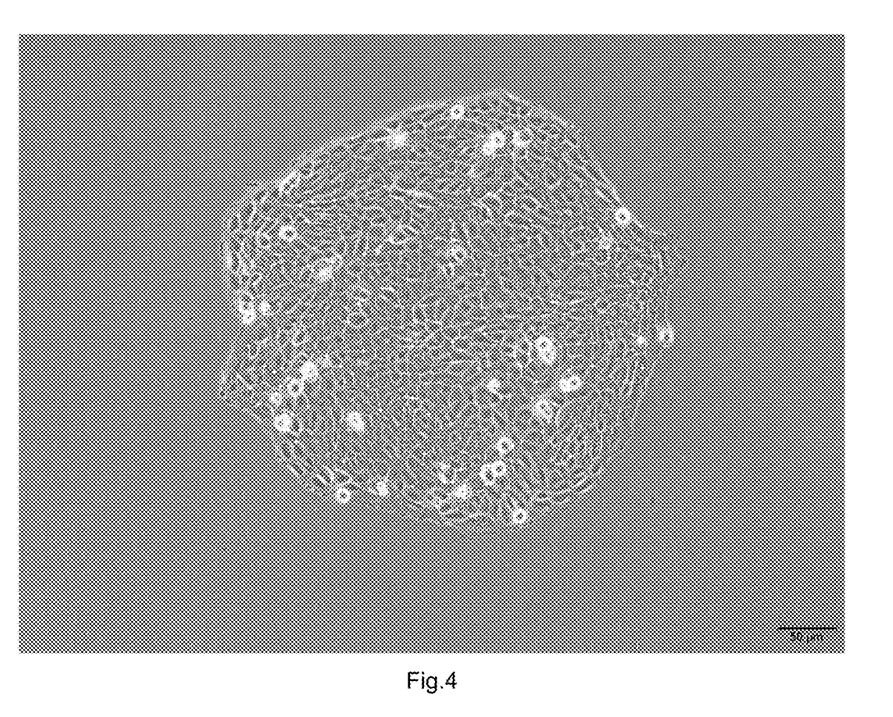
FIG. 4 is a schematic diagram of the HaCaT monoclonal cell (No. 10).
Figure 5:
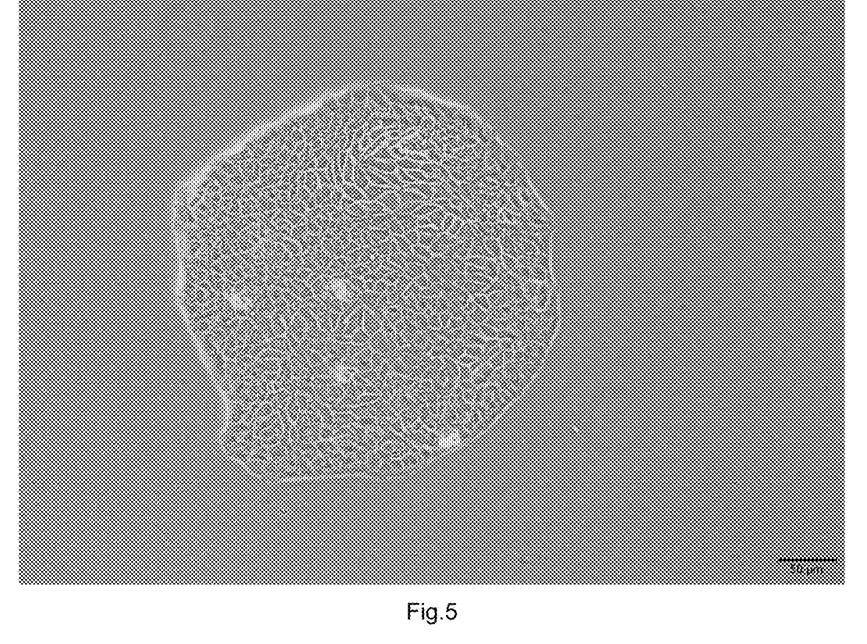
FIG. 5 is a schematic diagram of the HaCaT monoclonal cell (No. 38).
Figure 6:
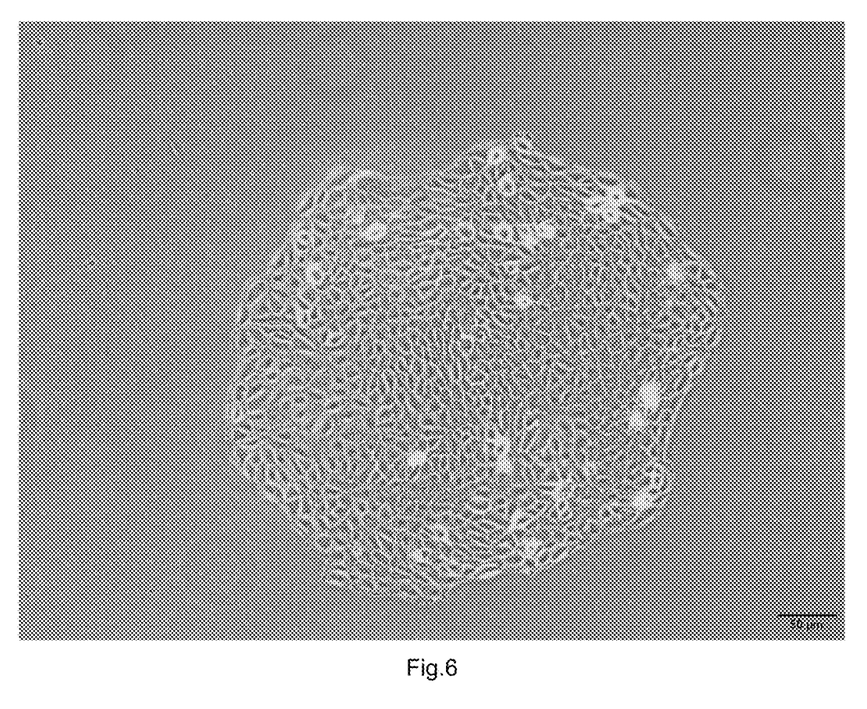
FIG. 6 is a schematic diagram of the HaCaT monoclonal cell (No. 43).
Figure 7:
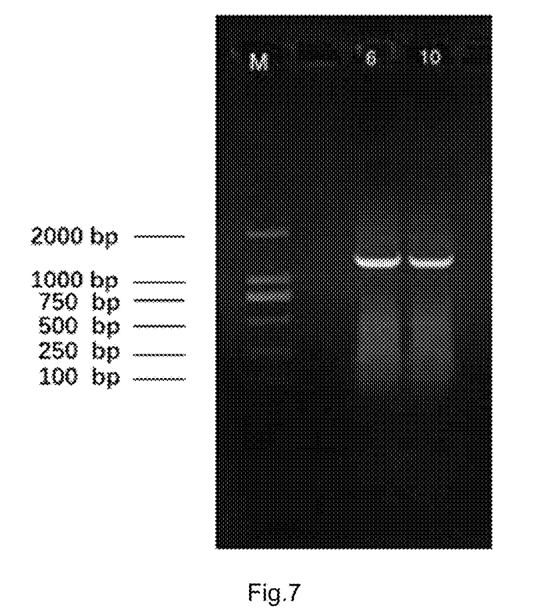
FIG. 7 shows the identification result of knocking a luciferase gene in the monoclone No. 6 and No. 10 by PCR.
Figure 8:
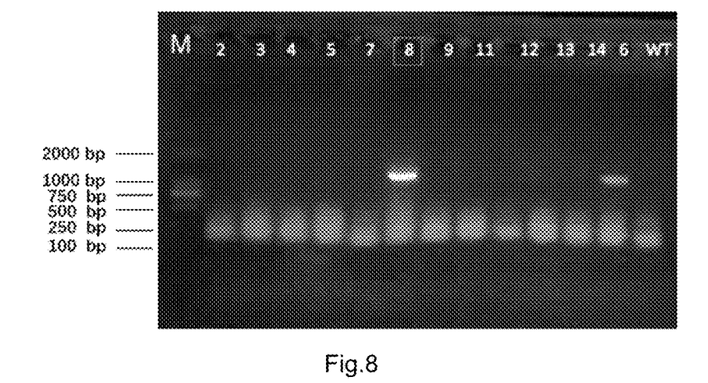
FIG. 8 shows the identification result of knocking a luciferase gene in the monoclone No. 8 by PCR.
Figure 9:
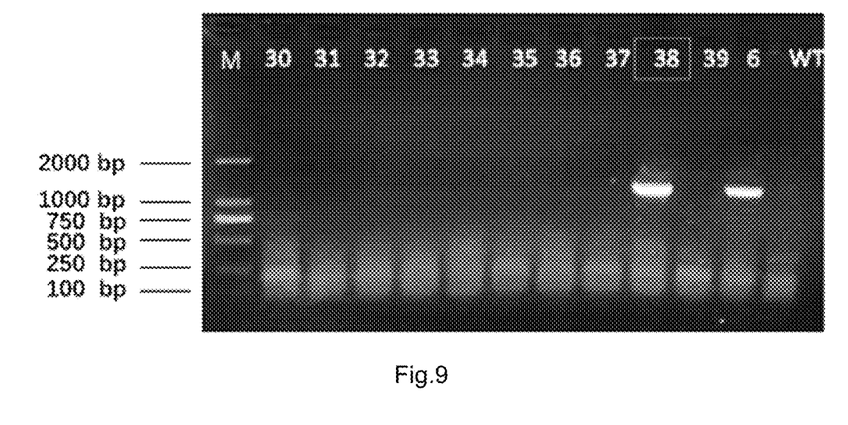
FIG. 9 shows the identification result of knocking a luciferase gene in the monoclone No. 38 by PCR.
Figure 10:
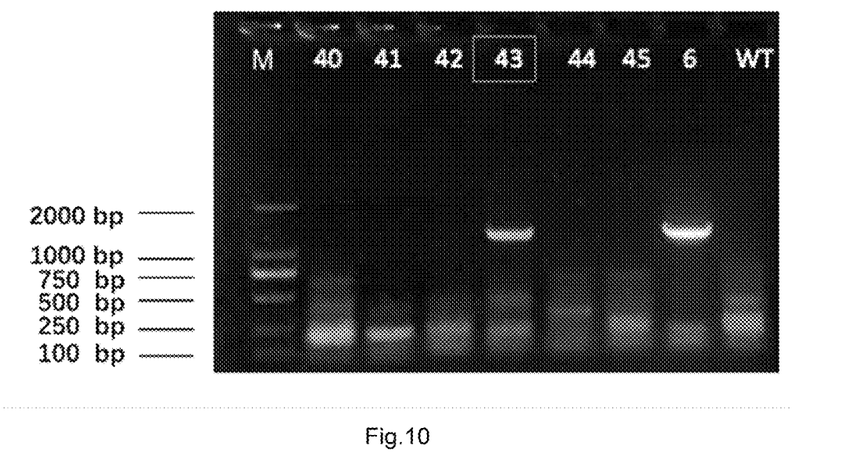
FIG. 10 shows the identification result of knocking a luciferase gene in the monoclone No. 43 by PCR.

The sequence of the sp6 primer was 5'-GATTTAGGTGACACTATAG-3' (SEQ ID NO: 5).

sgRNA-1, sgRNA-10, sgRNA-13 plasmid and hCas9 plasmid were co-transfected into 293T cells respectively. After 72 hours, the genome was extracted and expanded with the primers in Table 2 on the target site, and the PCR product was identified by T7EI digestion. Results showed that sgRNA-1 has four light bands, sgRNA-10 has two clear bands, and sgRNA-13 has four light bands as shown in FIG. 1, where sg1, sg10, and sg13 are sgRNA cleaved groups, WT is an uncleaved wild type and M is a DL2000 marker. FIG. 1 shows that the designed sgRNA-1 and sgRNA-13 can effectively cleave the target site.

Transfection of 293T Cells

The sgRNA-1, sgRNA-10, and sgRNA-13 plasmids were co-transfected into the 293T cells with a H-Cas9 plasmid (using liposome transfection), and the transfection steps were as follows:

(1) The prior medium was discarded, and 2 mL of fresh medium for incubation was added;

(2) 0.5 μg of the sgRNA recombinant plasmid and 0.5 μg of the hCas9 plasmid were dissolved in 100 μL of DMEM (H), 3 μL of a liposome transfection reagent was diluted to 100 μL, and the diluted liposome transfection reagent was added to the diluted plasmid solution. The mixture was gently blew evenly, formulated into a transfection complex, and reacted at room temperature for 15 min;

(3) The transfection complex was dropped into 6 wells, and reacted at 37° C. for 5 h. Then the reaction solution was discarded, and fresh medium was added for cultivation.

Genome Extraction Process (1) After transfection for 72 hours, 293T cells in 60 mm dish were all digested with 0.25% trypsin and centrifuged at 1000 rpm for 3 min, followed by discarding the supernatant;

(2) The cells were resuspended in 1 mL PBS, transferred to a 1.5 mL centrifuge tube, and centrifuged at 1000 rpm for 3 min followed by discarding the supernatant. Then 200 μL of PBS was added to suspend the cells;

(3) Genomic DNA was extracted by genomic extraction kit, and finally eluted with 40 μL of ddH$_2$O;

(4) Concentration of the DNA was determined;

(5) 1% agarose gel electrophoresis was carried out on the genomic DNA.

Amplification on the Target Site

PCR amplification of sgRNA-1, sgRNA-10, and sgRNA-13 was carried out using the extracted genome after transfection as a template; PCR amplification was performed using the wild type (WT) as a template and primers with SEQ ID NO: 6-7 as shown in Table 2.

TABLE 2

| PCR amplification primers | | |
|---|---|---|
| Primer name | Primer Sequence (5'-3') | Product size (bp) |
| HMOX1-sgRNA-JD-F | TGTTTTCACAATGTGGCCTGG | 578 |
| HMOX1-sgRNA-JD-R | CCATTGCCTGGATGTGCTTT | |

PCR amplification reaction procedure: 95° C. for 3 min; 95° C. for 45 s, 61° C. for 45 s, 72° C. for 30 s, 30 cycles; 72° C. for 5 min; storage under 4° C.

Identification after T7EI Digestion:

(1) 200 ng of the PCR product was diluted to 20 μL for denaturation and annealing, wherein the procedure were as follows: 95° C., 5 min; 95-85° C. at −2° C./s; 85-25° C. at −0.1° C./s; Hold at 4° C.

(2) 0.2 μL of T7EI was added to the 20 μL system to allow digestion at 37° C. for 30 minutes. Then 2 μL of 10×loading buffer was added and 2% agarose gel electrophoresis was carried out for identification.

2. Using pcDNA3.1(−) (Invitrogen) as a backbone, a luciferase gene linked to a T2A peptide sequence was inserted between the homologous left arm (500 bp, SEQ ID NO: 4 from No. 934 base to No. 1433 base counting from the 5' end) and the homologous right arm (800 bp, SEQ ID NO: 4 from No. 3138 base to No. 3937 base counting from the 3' end) (where the homologous left arm is a sequence 500 bp upstream from the No. 17529 base (inclusive) of NG_023030, and the homologous right arm is a sequence 800 bp downstream from the No. 17530 base (inclusive) of NG_023030), and a homologous recombinant vector was obtained with a sequence as shown in SEQ ID NO: 4. The specific method is as follows:

(1) using the wild type genome as a template and the primers in Table 3, with SEQ ID NO: 8-9, a fragment containing the homologous left arm and the homologous right arm was amplified;

(2) The luciferase gene on pGL4.10 (Promega) (with a sequence of No. 1488 base to No. 3137 base counting from the 5' end of SEQ ID NO: 4) was ligated to the T2A peptide sequence (SEQ ID NO:4 No. 1434 base to No. 1487 base counting from the 5' end) to recombine homologously between the homologous left arm and the homologous right arm;

(3) A NotI/BamHI restriction site was added to the homologous left arm-T2A-luciferase gene-the homologous right arm fragment, which was in turn ligated to a Not-I/BamHI-digested linearized pcDNA3.1(−) vector. The ligation product was transformed, plasmid extracted, and verified by sequencing analysis.

TABLE 3

Primers for amplification of the fragment containing the homologous left arm and the homologous right arm

| Primer name | Primer sequence (5'-3') | Product size (bp) |
|---|---|---|
| HMOX1-LR-F | AACCAGGGATGGGACTGAAC | 1652 |
| HMOX1-LR-R | TCGCCCACCAGCTACTTAAA | |

3. Construction and identification of targetedly knocking the luciferase gene into the HMOX1 gene in a HaCaT monoclonal cell The constructed sgRNA-13 plasmid, luciferase gene homologous recombination vector and hCas9 plasmid were co-transfected into HaCaT cells. After 72 hours, 800 µg/mL G418 (geneticmycin) was added for screening. The reagent was changed once every 2 days, and the cells were digested after 7 days followed by limited dilution. The cells were plated in five 10 cm plates at a density of 100 cells per well, and the cells were picked up after about 15 days when the monoclonal cells were grown to about 0.5 cm. 45 monoclonal cells were picked and cultured in 24-well plates. After overgrown, 1/10 of the cells were used to identify genotypes, and 9/10 of the cells were transferred to 12-well plates for expansion, which were frozen for storage after they were overgrown. According to the sequencing analysis, a series of monoclonal knock-in cells were obtained, which were clones No. 6, No. 8, No. 10, No. 38 and No. 43 (see FIG. 2, FIG. 3, FIG. 4, FIG. 5, FIG. 6).

Figure 11:
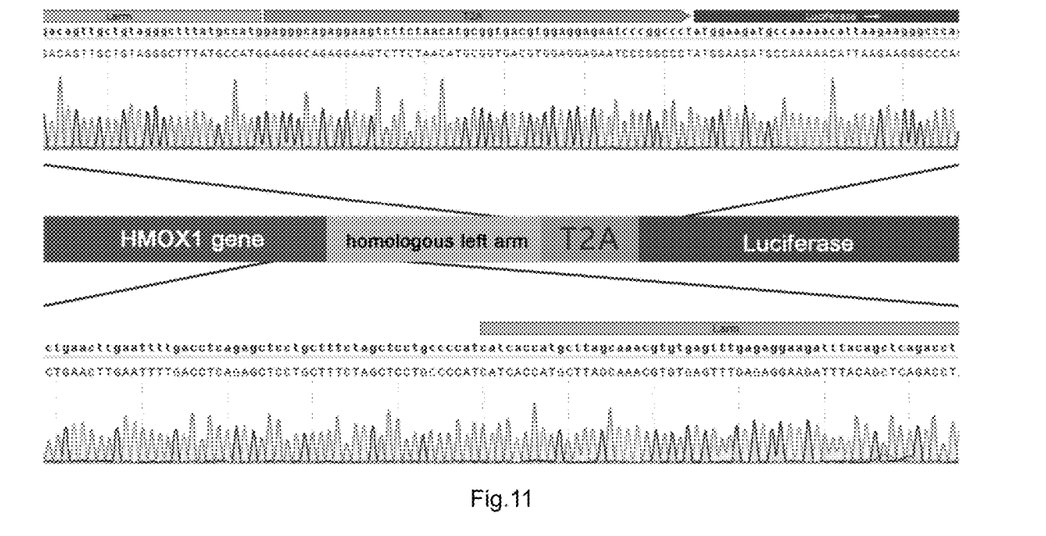
FIG. 11 shows the sequencing analysis result of knocking a luciferase gene in the monoclone No. 38.

After the monoclonal cells were expanded and cultured, PCR amplification and sequencing analysis were performed using the primers with SEQ ID NOs: 10 to 11 in Table 4, respectively. The identification results are shown in FIG. 7 to FIG. 10. Results shows that the clones No. 6, No. 8, No. 10, No. 38, No. 43 have a target band, and the luciferase gene was inserted into the genome; FIG. 11 shows the result of the sequencing analysis of No. 38 monoclonal genomic PCR product, which proves the correctness of the sequence.

TABLE 4

PCR amplification primers

| Primer name | Primer sequence (5'-3') | Product size (bp) |
|---|---|---|
| HMOX1-HRL-F | CAGGTGGCACATCTACCCAG | 1248 |
| HMOX1-HRL-R | GCAAGCTATTCTCGCTGCAC | |

4. Analysis of sensitization of compounds after gene knock-in Sensitization of compounds was detected using clone No. 38.

Figure 12:
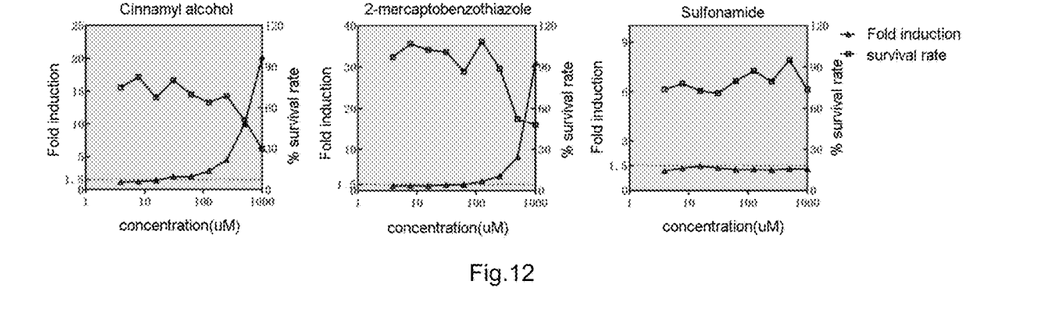
FIG. 12 shows the results of detecting sensitization of cinnamyl alcohol, 2-mercaptobenzothiazole, and sulfonamide by No. 38 monoclone.

(1) A sensitizing compound cinnamyl alcohol was selected for the experiment. The luciferase expression assay and MTT activity assay results are shown in FIG. 12. Compared with the negative control group, the constructed cell model exhibited increased expression of luciferase after the addition of cinnamyl alcohol; and the expression of luciferase and cinnamyl alcohol concentration showed quantitative relationship, with increasing cinnamyl alcohol concentration, the expression of luciferase reached up to 21 fold within the detection range of concentration (4 µM~1000 µM).

(2) A sensitizing compound 2-mercaptobenzothiazole was selected for the experiment. The results of luciferase expression assay and MTT activity assay are shown in FIG. 12. Compared with the negative control group, the constructed cell model exhibited increased expression of luciferase after the addition of 2-mercaptobenzothiazole; and the expression of luciferase and 2-mercaptobenzothiazole concentration showed quantitative relationship, with increasing 2-mercaptobenzothiazole concentration, the expression of luciferase reached up to 30 fold within the detection range of concentration (4 µM~1000 µM).

(3) A non-sensitizing compound sulfonamide was selected for the experiment. The results of luciferase expression assay and MTT activity assay are shown in FIG. 12. Compared with the negative control group, the constructed cell model exhibited no significantly changed expression of luciferase after the addition of sulfonamide.

Administration Process:

Pre-cultured cells were centrifuged followed by removal of the supernatant, and were resuspended in fresh complete medium. The cell concentration was calculated with a cell counter after dilution for 10 times, and finally was adjusted to 50,000 cells/well. 200 µL of the cell solution was added to each well of a white opaque 96-well plate to ensure that the number of cells per well was substantially the same. The cell was incubated for 24 h at 37° C. in a 5% $CO_2$ incubator. After 24 h, the medium was removed, and a working solution was prepared with 1% FBS medium. The working solution was diluted to 50% each time from 1000 µM to obtain 9 concentrations, then 200 µL of the working solution was added to each well, and a negative control was provided. The DMSO concentration in the working solution was 0.5%. 1 to 2 drops of paraffin oil was added to each well and the cells were incubated for 48 hours. After 48 h, luciferase expression was measured and cell viability was detected using MTT.

Luciferase Detection Process:

(1) 48 hours after treatment, the medium containing the reagent was discarded, and the plate was washed twice with PBS;

(2) 100 µL of PBS was added to each well, and then an equal volume of the luciferase substrate was added;

(3) The plate was shaken at 200 rpm for 2 min to fully lyse the cells;

(4) A Tecan Infinite® 200 Pro multi-function microplate reader selecting luminescence, integration 0.5s was used and the reading was recorded.

MTT Assay for Cell Activity:

(1) 48 hours after treatment, the medium containing the reagent was discarded, the plate was washed twice with PBS and 200 µL of fresh 1% FBS medium was added;

(2) 27 µL of MTT solution was added to each well and the cells were incubated in an incubator for 4 h;

(3) After the incubation, the medium was carefully removed with a 1 mL syringe without removing the purple crystal at the bottom of the well, so as not to affect the experimental results. The cells were lysed by adding 200 µL of DMSO and shaking at 250 rpm for 5 min, and the purple crystals were sufficiently dissolved.

(4) The absorbance at OD 570 nm was measured by a Tecan Infinite® 200 Pro multi-function microplate reader.

Calculation Method:

A. Calculation of fold induction $$\text{Fold induction} = (L_{sample} - L_{blank})/(L_{solvent} - L_{blank});$$

wherein:

$L_{sample}$: fluorescence reading of the sample;
$L_{blank}$: blank fluorescence reading (without cells and sample);
$L_{solvent}$: mean fluorescence reading of solvent control (negative control).

B. Cell viability calculation (viability)

$$\text{Cell viability} = [(V_{sample} - V_{blank})/(V_{solvent} - V_{blank})]*100;$$

wherein:

$V_{sample}$: MTT absorption of the sample;
$V_{blank}$: MTT absorption of the blank (without cells and sample);
$V_{solvent}$: MTT absorption of the solvent control (negative control).

The above embodiments are preferred embodiments of the present invention, but the embodiments of the present invention are not limited to the above embodiments, and any other changes, modifications, substitutions, combinations, and simplifications made without departing from the spirit and scope of the invention should all be equivalent replacements and are included in the scope of the present invention.

The invention claimed is:

1. A method for constructing a cell model where a reporter gene is knocked into a specific site on a HMOX1 gene mediated by CRISPR/CAS9, characterized by comprising the following steps:

(1) constructing an sgRNA expression vector, in which the sgRNA is specific for a target site on the HMOX1 gene based on CRISPR/Cas9 vector system, and a DNA target sequence of the sgRNA is as shown by SEQ ID NO: 1 or SEQ ID NO: 3;

(2) constructing a homologous recombinant vector in which a reporter gene linked to a self-cleaving peptide sequence is knocked into a specific site of the expression frame of the HMOX1 gene; and the specific site is located between No. 17529 base and No. 17530 base of the HMOX1 gene; and (3) co-transfecting the homologous recombinant vector, an hCas9 plasmid and the sgRNA expression vector into a mammalian keratinocyte, a mammalian dendritic cell or a mammalian monocyte, and carrying out monoclonal expansion to obtain the cell model where a reporter gene is knocked into the specific site on the HMOX1 gene mediated by CRISPR/CAS9.

2. The method for constructing a cell model where a reporter gene is knocked into the specific site on the HMOX1 gene mediated by CRISPR/CAS9 according to claim 1, characterized in that:

in step (1), the sgRNA is expressed using U6 promoter, and the sgRNA is used to synthesize an oligo to construct the sgRNA expression vector.

3. The method for constructing a cell model where a reporter gene knocked into the specific site on the HMOX1 gene mediated by CRISPR/CAS9 according to claim 1, characterized in that:

the reporter gene in step (2) is one of a luciferase gene, a chloramphenicol acetyltransferase gene, a β-galactosidase gene or a dihydrofolate reductase gene.

4. The method for constructing a cell model where a reporter gene is knocked into the specific site on the HMOX1 gene mediated by CRISPR/CAS9 according to claim 1, characterized in that:

the self-cleaving peptide in step (2) is one of a T2A peptide, an E2A peptide, an F2A peptide or a P2A peptide.

5. The method for constructing a cell model where a reporter gene is knocked into the specific site on the HMOX1 gene mediated by CRISPR/CAS9 according to claim 1, characterized in that:

the sequence of the homologous recombinant vector in step (2) is as shown by SEQ ID NO: 4.

6. The method for constructing a cell model where a reporter gene is knocked into the specific site on the HMOX1 gene mediated by CRISPR/CAS9 according to claim 1, characterized in that:

the mammalian keratinocyte in step (3) is a HaCaT cell;
the mammalian dendritic cell in step (3) is a CD34-derived dendritic cell; and
the mammalian monocyte in step (3) is a THP-1 cell.

7. A cell model where a reporter gene is knocked into the specific site on the HMOX1 gene mediated by CRISPR/CAS9, characterized by being obtained through the constructing method of claim 1.

* * * * *

SEQUENCE LISTING

```
<160> NUMBER OF SEQ ID NOS: 11

<210> SEQ ID NO 1
<211> LENGTH: 23
<212> TYPE: DNA
<213> ORGANISM: Artificial Sequence
<220> FEATURE:
<223> OTHER INFORMATION: sgRNA-1

<400> SEQUENCE: 1
ttaacaggtg ggcgtgcatc agg                                            23

<210> SEQ ID NO 2
<211> LENGTH: 23
<212> TYPE: DNA
<213> ORGANISM: Artificial Sequence
<220> FEATURE:
<223> OTHER INFORMATION: sgRNA-10

<400> SEQUENCE: 2
ggtccttaca ctcagctttc tgg                                            23

<210> SEQ ID NO 3
<211> LENGTH: 23
<212> TYPE: DNA
<213> ORGANISM: Artificial Sequence
<220> FEATURE:
<223> OTHER INFORMATION: sgRNA-13

<400> SEQUENCE: 3
gctttatgcc atgtgaatgc agg                                            23

<210> SEQ ID NO 4
<211> LENGTH: 8388
<212> TYPE: DNA
<213> ORGANISM: Artificial Sequence
<220> FEATURE:
<223> OTHER INFORMATION: Sequence of the homologous recombinant vector

<400> SEQUENCE: 4
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
```

```
attgacgtca atgggtggag tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta caactccgc cccattgacg caaatgggcg       780
gtaggcgtgt acggtgggag gtctatataa gcagagctct ctggctaact agagaaccca      840
ctgcttactg gcttatcgaa attaatacga ctcactatag ggagacccaa gctggctagc      900
gtttaaacgg gccctctaga ctcgagcggc cgccatcacc atgcttagca aacgtgtgag      960
tttgagagga agatttacag ctcagaccta attgctggca agtttaagg agaggacagg      1020
gagcaggcag aagtctgaaa accacgcctg ggcccaagaa tgttttcaca atgtggcctg      1080
gctgcacagg gaagaacaga cagcttgaag aagtagtgag ctgcccgtct ttgaaggtat      1140
tcaagcagtg gctagaggga cacctgtctg tggtcttgca gaatcctggc gttgggcagt      1200
gactgtacca cagaccctga ggccgctctg ctttgctttc ctatgacatc agacaccctg      1260
atgcacgccc acctgttaat gaccttgccc cattttctct ttcagattct gccccgtgg      1320
agactcccag agggaagccc ccactcaaca cccgctccca ggctccgctt ctccgatggg      1380
tccttacact cagcttctg gtggcgcagag ttgctgtagg gctttatgcc atggagggca     1440
gaggaagtct tctaacatgc ggtgacgtgg aggagaatcc cggccctatg aagatgcca       1500
aaaacattaa gaagggcccca cgccattct acccactcga agacgggacc gccggcgagc      1560
agctgcacaa agccatgaag cgctacgccc tggtgcccgg caccatcgcc tttaccgacg      1620
cacatatcga ggtggacatt acctacgccg agtacttcga gatgagcgtt cggctggcag      1680
aagctatgaa gcgctatggg ctgaatacaa accatcggat cgtggtgtgc agcgagaata      1740
gcttgcagtt cttcatgccc gtgttgggtg ccctgttcat cggtgtggct gtggccccag      1800
ctaacgacat ctacaacgag cgcgagctgc tgaacagcat gggcatcagc cagcccaccg      1860
tcgtattcgt gagcaagaaa gggctgcaaa agatcctcaa cgtgcaaaag aagctaccga      1920
tcatacaaaa gatcatcatc atggatagca agaccgacta ccagggcttc caaagcatgt      1980
acaccttcgt gacttcccat ttgccacccg gcttcaacga gtacgacttc gtgcccgaga      2040
gcttcgaccg ggacaaaacc atcgccctga tcatgaacag tagtggcagt accggattgc      2100
ccaagggcgt agccctaccg caccgcaccg cttgtgtccg attcagtcat gcccgcgacc      2160
ccatcttcgg caaccagatc atccccgaca ccgctatcct cagcgtggtg ccatttcacc      2220
acggcttcgg catgttcacc acgctgggct acttgatctg cggctttcgg gtcgtgctca      2280
tgtaccgctt cgaggaggag ctattcttgc gcagcttgca agactataag attcaatctg      2340
ccctgctggt gcccacacta tttagcttct tcgctaagag cactctcatc gacaagtacg      2400
acctaagcaa cttgcacgag atcgccagcg gcggggcgcc gctcagcaag gaggtaggtg      2460
aggccgtggc caaacgcttc cacctaccag gcatccgcca gggctacggc ctgacagaaa      2520
caaccagcgc cattctgatc accccgaag gggacgacaa gcctggcgca gtaggcaagg      2580
tggtgccctt cttcgaggct aaggtggtgg acttggacac cggtaagaca ctgggtgtga      2640
accagcgcgg cgagctgtgc gtccgtggcc ccatgatcat gagcggctac gttaacaacc      2700
ccgaggctac aaacgctctc atcgacaagg acggctggct gcacagcggc gacatcgcct      2760
actgggacga ggacgagcac ttcttcatcg tggaccggct gaagagcctg atcaaataca      2820
```

```
agggctacca ggtagcccca gccgaactgg agagcatcct gctgcaacac cccaacatct    2880
tcgacgccgg ggtcgccggc ctgcccgacg acgatgccgg cgagctgccc gccgcagtcg    2940
tcgtgctgga acacggtaaa accatgaccg agaaggagat cgtggactat gtggccagcc    3000
aggttacaac cgccaagaag ctgcgcgtgt gtgttgtgtt cgtggacgag gtgcctaaag    3060
gactgaccgg caagttggac gcccgcaaga tccgcgagat tctcattaag gccaagaagg    3120
gcggcaagat cgccgtgtga atgcaggcat gctggctccc agggccatga actttgtccg    3180
gtggaaggcc ttctttctag agagggaatt ctcttggctg gcttccttac cgtgggcact    3240
gaaggctttc agggcctcca gccctctcac tgtgtccctc tctctggaaa ggaggaagga    3300
gcctatggca tcttccccaa cgaaaagcac atccaggcaa tggcctaaac ttcagagggg    3360
gcgaagggat cagccctgcc cttcagcatc ctcagttcct gcagcagagc ctggaagaca    3420
ccctaatgtg gcagctgtct caaacctcca aaagccctga gtttcaagta tccttgttga    3480 cacgccatg accactttcc ccgtgggcca tggcaatttt tacacaaacc tgaaaagatg    3540
ttgtgtcttg tgttttttgtc ttattttttgt tggagccact ctgttcctgg ctcagcctca    3600
aatgcagtat ttttgttgtg ttctgttgtt tttatagcag ggttggggtg gttttttgagc    3660 catgcgtggg tggggaggga ggtgtttaac ggcactgtgg ccttggtcta acttttgtgt    3720
gaaataataa acaacattgt ctgatagtag cttgaagtag ttttcatggg ctttgttatt    3780
cttggggaac tgacctttc ctccctggtt tcttgcgtgc tcggtaggag aagtggtgat    3840 aggggggttgg caggagctgg tctgtttgag aatacagaag gtgagctttt cttttctttt    3900 ttttttttttt tgagatggag tctcactctg tcacccagga tccgagctcg gtaccaagct    3960
taagtttaaa ccgctgatca gcctcgactg tgccttctag ttgccagcca tctgttgttt    4020
gcccctcccc cgtgccttcc ttgaccctgg aaggtgccac tcccactgtc ctttcctaat    4080
aaaatgagga aattgcatcg cattgtctga gtaggtgtca ttctattctg ggggtgggg    4140 tggggcagga cagcaagggg gaggattggg aagacaatag caggcatgct ggggatgcgg    4200
tgggctctat ggcttctgag gcggaaagaa ccagctgggg ctctagggg tatccccacg    4260 cgccctgtag cggcgcatta agcgcggcgg gtgtggtggt tacgcgcagc gtgaccgcta    4320
cacttgccag cgccctagcg cccgctcctt tcgctttctt cccttccttt ctcgccacgt    4380
tcgccggctt tccccgtcaa gctctaaatc ggggggctccc tttagggttc cgatttagtg    4440
ctttacggca cctcgacccc aaaaaacttg attagggtga tggttcacgt agtgggccat    4500
cgccctgata gacggttttt cgccctttga cgttggagtc cacgttcttt aatagtggac    4560
tcttgttcca aactggaaca acactcaacc ctatctcggt ctattctttt gatttataag    4620
ggattttgcc gatttcggcc tattggttaa aaaatgagct gatttaacaa aaatttaacg    4680
cgaattaatt ctgtggaatg tgtgtcagtt agggtgtgga aagtccccag gctccccagc    4740
aggcagaagt atgcaaagca tgcatctcaa ttagtcagca accaggtgtg gaaagtcccc    4800
aggctcccca gcaggcagaa gtatgcaaag catgcatctc aattagtcag caaccatagt    4860
cccgccccta actccgccca tcccgcccct aactccgccc agttccgccc attctccgcc    4920
ccatggctga ctaatttttt ttatttatgc agaggccgag gccgcctctg cctctgagct    4980
attccagaag tagtgaggag gcttttttgg aggcctaggc ttttgcaaaa agctcccggg    5040
agcttgtata tccatttcg gatctgatca agagacagga tgaggatcgt ttcgcatgat    5100
tgaacaagat ggattgcacg caggttctcc ggccgcttgg gtggagaggc tattcggcta    5160
```

-continued

```
tgactgggca caacagacaa tcggctgctc tgatgccgcc gtgttccggc tgtcagcgca   5220
ggggcgcccg gttcttttg tcaagaccga cctgtccggt gccctgaatg aactgcagga    5280
cgaggcagcg cggctatcgt ggctggccac gacgggcgtt ccttgcgcag ctgtgctcga   5340
cgttgtcact gaagcgggaa gggactggct gctattgggc gaagtgccgg ggcaggatct   5400
cctgtcatct caccttgctc ctgccgagaa agtatccatc atggctgatg caatgcggcg   5460
gctgcatacg cttgatccgg ctacctgccc attcgaccac caagcgaaac atcgcatcga   5520
gcgagcacgt actcggatgg aagccggtct tgtcgatcag gatgatctgg acgaagagca   5580 tcagggctc cgccagccg aactgttcgc caggctcaag gcgcgcatgc ccgacgcgca    5640
ggatctcgtc gtgacccatg gcgatgcctg cttgccgaat atcatggtgg aaaatggccg   5700
cttttctgga ttcatcgact gtggccggct gggtgtggcg gaccgctatc aggacatagc   5760
gttggctacc cgtgatattg ctgaagagct tggcggcgaa tgggctgacc gcttcctcgt   5820
gctttacggt atcgccgctc ccgattcgca gcgcatcgcc ttctatcgcc ttcttgacga   5880
gttcttctga gcgggactct ggggttcgaa atgaccgacc aagcgacgcc caacctgcca   5940
tcacgagatt tcgattccac cgccgccttc tatgaaaggt tgggcttcgg aatcgttttc   6000
cgggacgccg gctggatgat cctccagcgc ggggatctca tgctggagtt cttcgcccac   6060
cccaacttgt ttattgcagc ttataatggt tacaaataaa gcaatagcat cacaaatttc   6120
acaaataaag cattttttc actgcattct agttgtggtt tgtccaaact catcaatgta    6180
tcttatcatg tctgtatacc gtcgacctct agctagagct tggcgtaatc atggtcatag   6240
ctgtttcctg tgtgaaattg ttatccgctc acaattccac acaacatacg agccggaagc   6300
ataaagtgta aagcctgggg tgcctaatga gtgagctaac tcacattaat tgcgttgcgc   6360
tcactgcccg ctttccagtc gggaaacctg tcgtgccagc tgcattaatg aatcggccaa   6420 cgcgcggga gaggcggttt gcgtattggg cgctcttccg cttcctcgct cactgactcg   6480
ctgcgctcgg tcgttcggct gcggcgagcg gtatcagctc actcaaaggc ggtaatacgg   6540
ttatccacag aatcagggga taacgcagga agaacatgt gagcaaaagg ccagcaaaag    6600
gccaggaacc gtaaaaaggc cgcgttgctg gcgtttttcc ataggctccg ccccctgac    6660 gagcatcaca aaaatcgacg ctcaagtcag aggtggcgaa acccgacagg actataaaga   6720
taccaggcgt ttccccctgg aagctccctc gtgcgctctc ctgttccgac cctgccgctt   6780
accggatacc tgtccgcctt tctcccttcg ggaagcgtgg cgctttctca tagctcacgc   6840
tgtaggtatc tcagttcggt gtaggtcgtt cgctccaagc tgggctgtgt gcacgaaccc   6900
cccgttcagc ccgaccgctg cgccttatcc ggtaactatc gtcttgagtc aacccggta    6960 agacacgact tatcgccact ggcagcagcc actggtaaca ggattagcag agcgaggtat   7020
gtaggcggtg ctacagagtt cttgaagtgg tggcctaact acggctacac tagaagaaca   7080
gtatttggta tctgcgctct gctgaagcca gttaccttcg gaaaaagagt tggtagctct   7140
tgatccggca acaaaccac cgctggtagc ggttttttg tttgcaagca gcagattacg    7200
cgcagaaaaa aaggatctca agaagatcct ttgatctttt ctacggggtc tgacgctcag   7260
tggaacgaaa actcacgtta agggattttg gtcatgagat tatcaaaaag gatcttcacc   7320
tagatccttt taaattaaaa atgaagtttt aaatcaatct aaagtatata tgagtaaact   7380
tggtctgaca gttaccaatg cttaatcagt gaggcaccta tctcagcgat ctgtctattt   7440
cgttcatcca tagttgcctg actccccgtc gtgtagataa ctacgatacg ggagggctta   7500
ccatctggcc ccagtgctgc aatgataccg cgagacccac gctcaccggc tccagattta   7560
```

```
tcagcaataa accagccagc cggaagggcc gagcgcagaa gtggtcctgc aactttatcc    7620
gcctccatcc agtctattaa ttgttgccgg gaagctagag taagtagttc gccagttaat    7680
agtttgcgca acgttgttgc cattgctaca ggcatcgtgg tgtcacgctc gtcgtttggt    7740
atggcttcat tcagctccgg ttcccaacga tcaaggcgag ttacatgatc ccccatgttg    7800
tgcaaaaaag cggttagctc cttcggtcct ccgatcgttg tcagaagtaa gttggccgca    7860
gtgttatcac tcatggttat ggcagcactg cataattctc ttactgtcat gccatccgta    7920
agatgctttt ctgtgactgg tgagtactca accaagtcat tctgagaata gtgtatgcgg    7980
cgaccgagtt gctcttgccc ggcgtcaata cgggataata ccgcgccaca tagcagaact    8040
ttaaaagtgc tcatcattgg aaaacgttct cggggcgaaa actctcaag gatcttaccg    8100 ctgttgagat ccagttcgat gtaacccact cgtgcaccca actgatcttc agcatctttt    8160
actttcacca gcgtttctgg gtgagcaaaa acaggaaggc aaaatgccgc aaaaaaggga    8220
ataagggcga cacggaaatg ttgaatactc atactcttcc ttttcaata ttattgaagc    8280 atttatcagg gttattgtct catgagcgga tacatatttg aatgtattta gaaaaataaa    8340
caaatagggg ttccgcgcac atttccccga aaagtgccac ctgacgtc                 8388
```

<210> SEQ ID NO 5
<211> LENGTH: 19
<212> TYPE: DNA
<213> ORGANISM: Artificial Sequence
<220> FEATURE:
<223> OTHER INFORMATION: sp6

<400> SEQUENCE: 5
gatttaggtg acactatag                                                   19

<210> SEQ ID NO 6
<211> LENGTH: 21
<212> TYPE: DNA
<213> ORGANISM: Artificial Sequence
<220> FEATURE:
<223> OTHER INFORMATION: HMOX1-sgRNA-JD-F

<400> SEQUENCE: 6
tgttttcaca atgtggcctg g                                                21

<210> SEQ ID NO 7
<211> LENGTH: 20
<212> TYPE: DNA
<213> ORGANISM: Artificial Sequence
<220> FEATURE:
<223> OTHER INFORMATION: HMOX1-sgRNA-JD-R

<400> SEQUENCE: 7
ccattgcctg gatgtgcttt                                                  20

<210> SEQ ID NO 8
<211> LENGTH: 20
<212> TYPE: DNA
<213> ORGANISM: Artificial Sequence
<220> FEATURE:
<223> OTHER INFORMATION: HMOX1-LR-F

<400> SEQUENCE: 8
aaccagggat gggactgaac                                                  20

<210> SEQ ID NO 9

```
<211> LENGTH: 20
<212> TYPE: DNA
<213> ORGANISM: Artificial Sequence
<220> FEATURE:
<223> OTHER INFORMATION: HMOX1-LR-R

<400> SEQUENCE: 9
tcgcccacca gctacttaaa                                              20

<210> SEQ ID NO 10
<211> LENGTH: 20
<212> TYPE: DNA
<213> ORGANISM: Artificial Sequence
<220> FEATURE:
<223> OTHER INFORMATION: HMOX1-HRL-F

<400> SEQUENCE: 10
caggtggcac atctacccag                                              20

<210> SEQ ID NO 11
<211> LENGTH: 20
<212> TYPE: DNA
<213> ORGANISM: Artificial Sequence
<220> FEATURE:
<223> OTHER INFORMATION: HMOX1-HRL-R

<400> SEQUENCE: 11
gcaagctatt ctcgctgcac                                              20
```